US006238906B1

(12) United States Patent
Salanitro

(10) Patent No.: US 6,238,906 B1
(45) Date of Patent: *May 29, 2001

(54) BIODEGRADATION OF ETHERS USING A BACTERIAL CULTURE

(75) Inventor: Joseph Patrick Salanitro, Houston, TX (US)

(73) Assignee: Shell Oil Company, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/292,037

(22) Filed: Apr. 14, 1999

Related U.S. Application Data

(63) Continuation-in-part of application No. 08/465,996, filed on Jun. 6, 1995, now Pat. No. 5,750,364.

(51) Int. Cl.$^7$ .............................. C12P 39/00; C12S 00/00
(52) U.S. Cl. ..................... 435/262.5; 435/42; 435/262; 435/821; 435/822; 210/610; 210/611; 210/620
(58) Field of Search ..................... 435/42, 262, 262.5, 435/821, 822; 210/610, 611, 620

(56) References Cited

U.S. PATENT DOCUMENTS

| 4,009,099 | * | 2/1977 | Jeris ..................................... 210/612 |
| 4,391,887 | * | 7/1983 | Baumgarten et al. ................. 435/42 |
| 4,415,454 | * | 11/1983 | Fuchs .................................... 210/616 |
| 5,474,934 | * | 12/1995 | Adamus et al. .................. 435/262.5 |
| 5,536,410 | * | 7/1996 | Kitatsjuji et al. .................... 210/626 |
| 5,750,364 | * | 5/1998 | Salanitro ............................... 435/42 |
| 5,811,010 | * | 9/1998 | Salanitro ............................. 210/610 |
| 5,814,514 | * | 9/1998 | Steffan et al. ....................... 435/262 |
| 5,902,734 | * | 5/1999 | Salanitro ............................... 435/42 |

OTHER PUBLICATIONS

"Characterization of MTBE–Degrading Bacterial Isolates and Associated Consortia", by Jessica Hanson and Kate Scow, presented at the MTBE Workshop on Jun. 16, 1998, pp. 1 of 1.
"Biodegradation of methyl t–butyl ether by pure bacaterial cultures", by K. Mo et al., Applied Microbiol Biotechnol. (1997)47:pp. 69–72.
K. Mo. et al.. Appli. Microbiol Biotechnol. (1997) 47:69–72.

* cited by examiner

Primary Examiner—Christopher R. Tate
(74) Attorney, Agent, or Firm—Y. Grace Tsang

(57) ABSTRACT

A bacterial culture capable of degrading ethers, especially branched alkylethers including MTBE, under aerobic conditions has been prepared.

6 Claims, No Drawings

BIODEGRADATION OF ETHERS USING A BACTERIAL CULTURE

This continuation-in-part of application Ser. No. 08/465,996 filed Jun. 6, 1995, now U.S. Pat. No. 5,750,364, the entire disclosure of which is hereby incorporated by reference.

FIELD OF THE INVENTION

This invention relates to a process for degrading ethers, such as methyl t-butyl ether (MTBE), utilizing a bacterial culture. This invention further relates to a bacterial culture capable of degrading ethers, including methyl t-butyl ether (MTBE), and the process for preparing such culture.

BACKGROUND OF THE INVENTION

Alkyl—alkyl ethers (R—O—R) such as methyl t-butyl ether (hereinafter "MTBE") are being used as octane-enhancers in the reformulation of low volatility unleaded gasoline blends and for reducing the emission of volatile organic compounds from engines. In general, alkylethers, especially those alkylethers which have only one ether linkage and without other functional groups, are chemically stable compounds and there is little information on their biodegradability in soil, groundwater and activated sludge environments. The lack of alkylether degradation by indigenous microbes in soils and biosludges may be attributed to the very stable and chemically unreactive ether linkage, the inability of these compounds to be transported into cells and/or the lack of inducible or existing enzyme activities (e.g. oxygenases, hydroxylases) which can attack the ether bond.

It is known that MTBE can persist in groundwater from accidental spills of unleaded gasoline from underground storage tanks. However, no known naturally-occurring microbial cultures exist to effectively biotreat groundwater, wastewater, tank bottom wastes or soils containing this ether.

Alkyl ethers such as symmetric dioctyl ether have been shown by Modrzakowski and Finnerty to be only partially oxidized by an Acinetobacter strain in which the ether linkage is not cleaved and only the terminal carbons are utilized for growth. See, Intermediary Metabolism of Acinetobacter Grown on Dialkyethers. *Can. J. Microbiol.*, 35:1031–1036 (1989).

Studies on the biodegradability testing of MTBE in sludges and soils by Fujiwara et al. showed that 100 ppm MTBE or diisopropylether (DIPE) does not degrade in activated sludge (300 ppm solids) in an oxygen uptake assay. Moreover, MTBE did not significantly affect the respiration rate of other hydrocarbons when blended (12% w/v) with the fuel. See, Fujiwara, T., T. Kinoshita, H. Sato and I. Kojima, Biodegradation And Bioconcentration of Alkyl Ethers, Yukagaku 33: 111–114 (1984).

Moller and Arvin proposed that MTBE (10 ppm) or TAME (t-amyl methyl ether, 3 ppm) were not degraded in 60 days by microbes in an aquifer soil, topsoil or activated sludges. In these experiments, MTBE at 200 ppm levels showed a weak inhibitory effect on the biodegradation of aromatic hydrocarbons (3.5 ppm BTEX). See, Moller, H. and E. Arvin, Solubility and Degradability of The Gasoline Additive MTBE, Methyl-tert-butyl-ether and Gasoline Compounds in Water, Contaminated Soil '90, 445–448 (1990), Kluwer Academic Publishers.

Recent studies by Suflita and Mormile on the anaerobic degradation of gasoline oxygenates in a landfill aquifer material showed that of several alkyl ethers tested (MTBE, TAME, ETBE, DIPE, ethyl ether, propyl ether) only n-butyl methyl ether was metabolized under anaerobic methanogenic conditions. MTBE is only cleaved under anaerobic condition to t-butyl alcohol which is not degraded further. See Suflita, J. M. and M. R. Mormile, Anaerobic Biodegradation of Known and Potential Gasoline Oxygenates in the Terrestrial Subsurface, *Environ. Sci. Technology* 27: 976–978 (1993).

Parales et al isolated an actinomycete from biosludge which was shown to grow on 1,4-dioxane could also utilize some of the linear alkyl ethers such as diethyl ether and methyl butyl ether, but not the branched alkyl ethers such as diisopropylether, ethyl t-butyl ether or ethylene glycol ethers. See, Parales, R. E., J. E. Admus, N. White, H.D. Degradation of 1,4-dioxane by an Actinomycete in Pure Culture, *Applied Environ Microbiol*, 60, 4527–4530, May, 1994.

Japanese patent application number 04,110,098, filed by Kyowa Hakko Kagyo KK, proposes the decomposition of ethylene glycol alkylethers with bacteria. The ethers decomposed have more than one ether linkages and/or have hydroxyl functional groups, which are known to be more readily degradable than those with only one ether linkage and without other functional groups.

Japanese patent application number 62,208,289, filed by Hodogaya Chem. Ind. KK, proposes the degradation of polyoxytetramethylene glycol with bacterial strains. The ethers degraded have multiple ether linkages and thus are more readily degradable than those with only one ether linkage and with no other functional groups.

Thus, there remains a need for a bacterial culture capable of degrading under aerobic condition an ether, especially an alkyl ether, more especially a branched alkyl ether such as MTBE. The culture would be useful for treating wastes and groundwater containing ethers, especially branched alkyl ethers such as MTBE.

SUMMARY OF THE INVENTION

This invention relates to (a) a bacterial culture capable of degrading alkylethers, especially branched alkylethers including MTBE, under aerobic conditions; (b) a process for preparing a bacterial culture which is capable of degrading alkylethers, especially branched alkylethers such as MTBE, to $CO_2$ using activated sludges; (c) a process for the aerobic degradation of ethers, especially branched alkylethers such as MTBE, using a bacterial culture prepared from activated sludges; (d) a process for remediating wastes and groundwater containing ethers, especially branched alkylethers such as MTBE, to reduce the alkylether(s) content thereof by growing in the presence of said wastes and groundwater a population of a bacterial culture prepared from activated sludges, particularly a pure bacterial culture; specifically a population of a culture derived from a mixed bacterial culture, more specifically a pure culture derived from a mixed bacterial culture. This invention further relates to a pure bacterial culture which degrades alkylethers, especially branched alkylethers including MTBE, under aerobic conditions to carbon dioxide and water; and a process for preparing such a pure bacterial culture from said mixed bacterial culture. This invention also relates to the use of said pure culture for degrading or remediating t-butyl alcohol containing aqueous solutions or groundwater.

DETAILED DESCRIPTION OF THE INVENTION

A culture of BC-1 has been deposited with the American Type Culture Collection (ATCC), Patent Depository, 12301

Parklawn Drive, Rockville, Md. 20852 with ATCC number 202057. A culture of BC-1, ATCC number 20205, can be obtained from the permanent collection of the ATCC, Patent Depository.

The present invention relates a bacterial culture capable of degrading a branched alkyl ether. Specifically, the present invention involves a pure bacterial culture capable of degrading aerobically a branched alkyl ether, particularly a tertiary carbon atom-containing alkyl ether, more particularly MTBE, to $CO_2$. The invention also relates to a mixed bacterial culture which degrades aerobically a branched alkyl ether, particularly a tertiary carbon atom-containing alkyl ether, more particularly MTBE, to $CO_2$. The bacterial culture(s) is capable of cleaving the ether linkage of methyl t-butyl ether (MTBE) with the transient formation of t-butyl alcohol (TBA) and degrading completely to $CO_2$. The novel bacterial culture can also metabolize other linear and branched ethers. Non-limiting and illustrative examples of the linear and branched ethers include diethyl ether (DEE), dimethyl ether (DME), methyl ethyl ether (MEE), methyl n-propyl ether (MPE), ethyl n-propyl ether, methyl isopropyl ether, ethyl isopropyl ether, diisopropyl ether (DIPE), ethyl t-butyl ether (ETBE) or methyl-t-amyl ether. Specifically, the invention relates to a novel mixed bacterial culture, designated BC-1 with ATCC No. 20257 which is capable of degrading MTBE completely to $CO_2$ with the transient formation of t-butyl alcohol (TBA).

As a more specific embodiment of the present invention, the novel mixed bacterial culture includes any composition derived from the mixed bacterial culture enriched from incubating activated sludge and a branched alkyl ether. Illustrative examples of the compositions derived from the mixed bacterial culture include, but not limited to, members of, fragments of bacterial culture, membrane fragments of bacterial culture, enzymes extracted and/or isolated from the bacterial culture, lyophilized and/or dried culture, lyophilized and/or dried fragments of culture, lyophilized and/or dried enzymes derived from said culture, bacterial culture and/or fragments thereof and/or enzymes derived therefrom bound to a carrier and/or binder and/or fixed bed, etc. Any method known to one skilled in art for making composition derived from the mixed culture including but not limited to extraction or fragmentation to obtain active ingredients/fragments thereof is within the scope of the present invention. As one non-limiting example of the present invention, the mixed culture can be first fragmented by sonification or lysing with lysozyme and/or a compound such as a chelating compound, followed by salting out the enzyme fractions using ammonium sulfate or NaCl.

As one specific aspect of aforementioned embodiment of the present invention, the composition derived from said mixed bacterial culture is a pure bacterial culture isolated from said mixed bacterial. As another specific aspect of the aforementioned embodiment of the present invention, the composition derived from said mixed bacterial culture is a composition derived from a pure culture isolated from the present mixed culture. Illustrative examples of the compositions derived from the pure bacterial culture include, but not limited to, members of, fragments of the bacterial culture, membrane fragments of bacterial culture, enzymes extracted and/or isolated from the bacterial culture, lyophilized and/or dried culture, lyophilized and/or dried fragments of culture, lyophilized and/or dried enzymes derived from said culture, bacterial culture and/or fragments thereof and/or enzymes derived therefrom bound to a carrier and/or binder and/or fixed bed, etc. Any method known to one skilled in art for making composition derived from a culture including but not limited to extraction or fragmentation to obtain active ingredients/fragments thereof is within the scope of the present invention.

The present invention also relates to a process for preparing the above-mentioned novel mixed bacterial culture by adding a branched alkyl ether such as MTBE to an activated sludge, specifically activated sludge obtained from chemical plant, petrochemical plant or a refinery, more specifically from a biotreater located in a wastewater treatment plant in a refinery or a petrochemical plant. As a specific embodiment of the present invention, the activated sludge is retrieved from the biotreater located in a wastewater treatment plant of a chemical plant. As a still more specific embodiment of the present invention, the activated sludge is retrieved from the biotreater of the South Effluent Treater for treating wastewater from the Chemical Plant of Shell Deer Park Manufacturing Complex located at 5900 Highway 225, Deer Park Tex. 77536.

The mixed culture is prepared by adding a branched alkyl ether to the biosludge (activated sludge) and incubating for a period time. As one specific embodiment of the present invention, the biosludge is first added to a mineral nutrient solution. One specific, but non-limiting, example of the mineral solution is Sturm solution comprising $KH_2PO_4$, $K_2HPO_4$, $Na_2HPO_4.2H_2O$, $MgSO_4.7H_2O$, $NH_4Cl$, $(NH_4)_2SO_4$, and $FeCl_3.6H_2O$. Incubation using other nutrient solution known to those skilled in the art is within the scope of the present invention. The concentration of the biosludge in the incubated medium (culture) can be any suitable amount which would produce sufficient concentration of ether degrading bacteria. In a specific embodiment of the present invention, from about 50 mg to about 5000 mg, more specifically from about 50 mg to about 1500 mg, still more specifically from about 300 to about 800 mg, of the biosludge solids are added to every liter of the incubation medium.

The above mixed culture is enriched by adding a suitable amount of branched alkyl ether. In a specific embodiment of the present invention, about 5–5000 mg, more specifically about 10–500 mg, still more specifically about 30–50 mg, of the branched alkyl ether is added to every liter of the culture (incubation medium or mixture).

The mixture or culture is incubated for a period of time. The typical temperature at which the culture is incubated ranges from about 5° C. to about 80° C., specifically from 10° C. to about 60° C., more specifically from about 15° C. to about 35° C., still more specifically from about 22° C. to about 25° C. Periodically, a sample of the culture (or supernatant) is withdrawn for branched alkyl ether analysis. A culture is active in degrading branched alkyl ether if there is detectable reduction of the concentration of the branched alkyl ether in the culture being enriched, after taken into account of the amount of branched alkyl ether evaporated. As an illustrative but non-limiting example, a culture which is considered very active in degrading branched alkyl ether will degrade a solution containing about 0.001–5000 ppm, more specifically about 0.01–500 ppm, still more specifically about 0.05–100 ppm, of branched alkyl ether by from about 10% to about 100%, specifically from about 30% to about 100%, more specifically from about 50% to about 100%, still more specifically from about 80% to about 100% in from about 2 hours to about 70 hours, specifically from about 2 hours to about 12 hours, more specifically from about 3 hours to about 5 hours. As an illustrative non-limiting example, a culture is capable of degrading a solution containing 120 mg/L of MTBE to close to 0 mg/L of MTBE in about 4 hours or less.

In one specific embodiment of the present invention, the mixture of the activated sludge and the mineral solution is first flushed with oxygen before the addition of the branched alkyl ether.

In still another specific embodiment of the present invention, periodically, a portion in an amount of about 5–80%, specifically about 10–70%, more specifically about 40–600%, of the supernatant of the culture is withdrawn and fresh mineral or nutrient solution is added to at least partially replace the amount of supernatant withdrawn. The withdrawal can be conducted at an interval of about 1–30 days, specifically 2–10 day, more specifically about 5–8 days.

As another specific embodiment of the present invention, multiple additions of branched alkyl ether are subsequently made to the culture (incubating medium) after the first addition of the branched alkyl ether. The subsequent additions were made at least two days after the first addition of the branched alkyl ether. As a specific aspect of this embodiment, sufficient amount of branched alkyl ether is added either immediately after each withdrawal of the supernatant or simultaneously with the addition of the replacement portion of mineral or nutrient solution, thereby compensating the loss of the branched alkyl ether resulted from the withdrawal. As another specific aspect of this embodiment, sufficient alkyl ether is added each time designed to maintain the alkyl ether concentration at about 50–150%, specifically about 80–120%, of the original concentration.

As a preferred embodiment of the present invention, multiple additions (re-inoculation) of the activated sludge is made to the culture periodically, such as at an interval of about 2–60 days, specifically about 3–30 days, more specifically about 5–10 days. In a specific aspect of this embodiment, from about 50 mg to about 5000 mg, more specifically from about 50 mg to about 1500 mg, still more specifically from about 300 to about 800 mg, of biosludge solids are added to every liter of the incubation medium at each re-inoculation.

Illustrative examples of the branched alkyl ether suitable for the enrichment of the culture to produce the culture of the present invention include, but not limited to, MTBE, diisopropyl ether, ethyl t-butyl ether, di-t-butyl ether, diisobutyl ether, isopropyl isobutyl ether, isopropyl t-butyl ether, isopropyl isobutyl ether, t-amyl methyl ether, t-amyl ethyl ether, t-amyl propyl ether, t-amyl isopropyl ether, t-amyl n-butyl ether, t-amyl isobutyl ether, t-amyl methyl ether, ethyl ether etc.

As a preferred embodiment of the present invention, methyl t-butyl ether (MTBE) is used in the enrichment of the bacterial culture to produce a MTBE degradable culture.

The enrichment process typically lasts from about 1 months to about one year, more typically from about 1.5 months to 5 months, more typically from about 2 months to about 4 months.

As a particular aspect of the present invention, it is provided with a process for isolating a pure culture from the present mixed bacterial culture. Any method known to one skilled in the art which is able to isolate the MTBE-degrading pure culture from the present mixed culture is within the scope of the present process. Non-limiting example of the process suitable for isolating the pure culture (s) of the present invention includes enhancing isolation of the pure microbe(s) degrading MTBE by first making dilution enrichments of the present mixed culture(s).

As a more preferred embodiment of the present invention, the culture produced is capable of degrading alkyl ethers, specifically branched alkyl ethers, more specifically MTBE, to carbon dioxide. The culture prepared can also be used to degrade t-butyl alcohol, isopropyl alcohol and acetone.

The present invention further involves a process for degrading ethers, including alkylethers and aromatic ethers utilizing the above-mentioned novel mixed culture and/or pure culture by contacting or growing the aforementioned culture or composition derived from the culture with or in a solution containing the ether to be degraded. The alkylethers include branched alkyl ether and linear alkyl ethers. Specifically, the process of the present invention is effective in degrading branched alkyl ether, particularly MTBE. As a specific embodiment of the present invention, the ether to be degraded can be an ingredient in an aqueous solution such as groundwater and wastewater, a solid mixture such as soil, etc. The degradation is preferably conducted under an oxygen-containing atmosphere, such as aerobic conditions. The degradation can be conducted at a temperature from about 5° C. to about 80° C., specifically from about 10° C. to about 60° C., more specifically from about 15° C. to about 35° C., still more specifically at ambient temperature.

As a specific embodiment of the present process, the bacterial culture is used to remediate groundwater and wastewater containing ether, specifically alkyl ether, more specifically MTBE.

It is known that when MTBE-containing fuels are accidentally released to the subsurface, this alkyl ether is the most water soluble and persistent compound in ground water. Other branched alkyl ethers which behave similarly and have also been considered by the oil industry as octane enhancers for motor fuels are diisopropyl ether (DIPE), ethyl tertiary butyl ether (ETBE) and methyl tertiary amyl ether (MTAE). The present invention thus provides an effective biological process for remediating these ethers accidentally released to the subsurface such as groundwater, wastewater and soil. In a specific embodiment of the present invention, the ethers can be completely mineralized to carbon dioxide by a suitable culture prepared by the aforementioned enrichment process. Hence, the remediation process can be substantially free of environmentally undesirable end products.

The present process is capable of degrading/remediating ether(s), specifically branched alkyl ether(s), more specifically MTBE, in an aqueous mixture containing from about 0.001 ppm to about 5000 ppm, specifically from about 0.01 ppm to about 500 ppm, more specifically from about 0.05 ppm to about 100 ppm of the ether(s); to reduce the content thereof by from about 10% to about 100%, specifically from about 30% to about 100%, more specifically from about 50% to about 100%, still more specifically from about 80% to about 100% in from about 2 hours to about 70 hours, specifically from about 2 hours to about 12 hours, more specifically from about 3 hours to about 5 hours, by growing in the aqueous mixture the culture of the present invention.

As a specific embodiment of the present invention, the isolated bacterial enrichment culture can cleave the ether linkage of MTBE with the transient formation of t-butylalcohol (TBA). The t-butylalcohol can be degraded by the culture to carbon dioxide. It can also metabolize other linear and branched ethers including diethyl ether (DEE), dimethyl ether (DME), methyl ethyl ether (MEE), methyl n-propyl ether (MPE), ethyl n-propyl ether, methyl isopropyl ether, ethyl isopropyl ether, diisopropyl ether (DIPE), ethyl t-butyl ether (ETBE) or methyl-t-amyl ether (MTAE), etc.

The invention will be illustrated by the following illustrative embodiments which are provided for illustration purpose only and are not intended to limit the scope of the instant invention.

ILLUSTRATIVE EMBODIMENTS

The following illustrative embodiments describe typical techniques of the present invention.

PART A: DERIVATION OF ETHER DEGRADABLE CULTURE

A-I: BC-1 ETHER DEGRADABLE MIXED CULTURE DERIVED FROM ACTIVATED SLUDGE FROM CHEMICAL PLANT BIOTREATER

The biosludge (activated sludge) used in this run (A-I) was retrieved from the biotreater of the South Effluent Treater for treating wastewater from the Chemical Plant of Shell Deer Park Manufacturing Complex located at 5900 Highway 225, Deer Park Tex. 77536. About 100–200 ml of the biosludge (activated sludge) containing about 300 to 800 mg of biosludge solids were added to 1 liter of Sturm solution containing the following minerals (in milligrams per liter, i.e. ppm) to form a culture in a 2-liter stirred glass vessel sealed with Viton O rings: $KH_2PO_4$, 17; $K_2HPO_4$, 44; $Na_2HPO_4.2H_2O$, 67; $MgSO_4.7H_2O$, 33; $NH_4Cl$, 3.4; $(NH_4)_2SO_4$, 40; $FeCl_3.6H_2O$, 1. Information on this mineral solution can be found in Sturm, R. N., Biodegradability of Nonionic Surfactants: Screening Test For Predicting Rate And Ultimate Degradation, *J. Am. Oil Chem. Soc.*, 50: 159–167 (1973).

The above culture was enriched by first flushing with oxygen for 5 minutes, followed by adding MTBE at an amount of about 30–50 mg MTBE per liter of the culture.

The culture was stirred continuously at room temperature (22–25° C.). At weekly intervals, 1–3 ml of the slurries were withdrawn and allowed to settle (or be filtered). The supernatant and samples (1–3 ml supernatant) withdrawn for MTBE analysis. At each sampling, the culture was enriched by removing 500 ml of supernatant medium and replacing with 500 ml of the sterile minerals solution containing 30–50 ppm MTBE. No significant reduction of MTBE concentration in the supernatants sampled was detected for about two months.

Starting two months after the commencement of the enrichment procedure, re-inoculation involving multiple additions of about 100–200 ml of the above-described activated-sludge retrieved from Shell Deer Park Chemical Plant biotreater was made to the culture about every 7–30 days for about two months. The above-mentioned enrichment procedure of periodic additions of MTBE and withdrawal of the supernatant was also continued.

After two months, this enriched culture became active in consistently degrading MTBE concentrations in the supernatant about 500i to about 100% in about 2–4 hours. This culture was subsequently designated BC-1.

A-II: CONTROL—1% NaCN

A vessel used as a control was prepared following the enrichment procedure described in A-I above using the same biosludge material, except sufficient NaCN was added so that the culture contains 1% NaCN. NaCN was used as a microbial respiration inhibitor to monitor any ether loss from volatilization.

Results:

The Control (A-II) showed less than 10% loss of ether from volatilization. Mixed culture made from A-I, subsequently designated BC-1 ATCC No.20257, consistently degraded MTBE.

Microscopic and Species Characteristics of BC-1 Culture

Microscopic examination of phase-contrast and gram-stained smears of BC-1 showed that it contains gram-positive filamentous species and several gram-negative smaller rod-shaped bacteria. Preliminary identification of colonies isolated on a minerals (Sturm solution) agar medium containing 200 ppm of MTBE indicate that BC-1 contains at least 4–5 organisms including species of coryneforms, Pseudomonas and Achromobacter. All of these isolates utilize acetate, but none have been shown to grow on MTBE as sole source of carbon.

PART B: MAINTENANCE AND ANALYSIS OF BC-1 IN A BENCH BIOTREATER

The BC-1 culture obtained from A-I above was placed into a four-liter capacity sealed glass vessel for continuous culture maintenance. A similar suspended solids recycle apparatus with aerator (4 L) and clarifier (1 L) has been described in Salanitro et al, Effects of Ammonia and Phosphate Limitation on the Activated Sludge Treatment of Calcium-Containing Waste, *Biotechnol. Bioeng.*, 25 513–523 (1983), with the exception that pure oxygen was used in place of air to provide aerobic conditions. Dissolved oxygen was monitored with a Leeds and Northrup 7932 meter and probe and maintained at 4–7 mg/liter (ppm) with an oxygen flow rate of 10 ml/min. MTBE (2% solution) was added continuously at a rate of 30–40 ml/day (150–200 mg/liter (ppm)) using a Watson-Marlow (Model 101U) peristaltic pump. The pH was kept at 7.2–7.5 by the infusion of 2 M NaOH solution from a Masterflex® peristaltic pump. The culture was also fed with a minerals solution (4 liters/day) consisting of NaCl (1,000 mb/liter), $NH_4CL$ (380 ppm), $KH_2PO_4$ (350 ppm), and $MgSO_4.7H_2O$ (30 ppm). The ether-degrading culture developed a stable nitrifying population under high $NH_4^+$ (380 mg/liter (ppm) $NH_4Cl$) or low $NH_4^+$ (65 mg/liter (ppm) $NH_4Cl$) conditions. Suspended solids removed from the unit included 35–40 ml/day from the aerator (intentionally wasted) and 8 to 48 mg/day from the effluent. This waste rate was equivalent to a 80–90 day cell residence time.

Influent and effluent samples from the continuous biotreater were analyzed for cell dry weight according to methods outlined in Standard Methods For The Examination of Water And Wastewater, 17th Ed. Method 5210-B, American Public Health Association, Washington, D.C. $NH_4^+$, $NO_3^-$ and $PO_4^{31\ 3}$ ions were estimated by routine Dionexm ion chromatography.

Data on the growth and metabolism of the BC-1 culture in the solids recycle culture are given in TABLE 1 below.

TABLE 1

Nitrification and Biomass Yields in BC-1 Continuous Culture Degrading MTBE

| Parameter[a] | Nitrifying Condition | |
|---|---|---|
| | High $NH_4^+$ | Low $NH_4^+$ |
| Influent $NH_4^+$, ppm | 120–125 | 10–20 |
| Effluent $NO_3^-$, ppm | 390–450 | 50–70 |
| Reactor TSS, ppm[b] | 2500–2580 | 2020–2340 |
| Solids retention, days | 80–90 | 80–85 |
| Average % MTBE removed | 80–90[c] | 60–65[d] |

TABLE 1-continued

Nitrification and Biomass Yields in BC-1
Continuous Culture Degrading MTBE

| | Nitrifying Condition | |
|---|---|---|
| Parameter[a] | High $NH_4^+$ | Low $NH_4^+$ |
| Cell yield, g TSS/g MTBE utilized | 0.21–.24 | 0.23–.28 |

[a] Analyses given are the average of four weeks data under each condition.
[b] Waste rates were 1.1–1.3 liters every four weeks; effluent TSS under both conditions varied from 2–12 ppm and contributed 25–30% of biomass loss from the unit.
[c] Influent and effluent MTBE varied from 160–210 ppm and 3–40 ppm, respectively.
[d] Influent and effluent MTBE varied from 120–175 ppm and 50–60 ppm, respectively.

PART C: BATCH SUBSTRATE REMOVAL EXPERIMENTS

The utilization of MTBE and t-butyl alcohol (TBA), a possible major metabolite of MTBE, was assessed in batch removal assays with BC-1. In this test, individual compounds were added (120–130 ppm) to one liter of BC-1 culture in a 1.5 liter vessel. Before addition of each compound, the culture was flushed with sterile 100% $O_2$ in a 1.5 liter sealed vessel for 2–5 minutes to achieve a dissolved oxygen level of 20 ppm. The reaction vessel was stirred continuously at 22–25° C. and the depletion of substrates monitored by sampling (2–3 ml) over a 24 hours period. MTBE and TBA were analyzed by methods described below.

Analysis of MTBE and TBA

Culture samples were analyzed for MTBE and t-butanol using a Hewlett-Packard Model 280 gas chromatography-flame ionization detection system. Compounds were separated on a Quadrex methyl silicone (1-Fm-thick film) capillary column having dimensions 25 m long and 0.025 mm inside diameter. Alltech/Applied Science Labs, State College, Pa.). The column was set initially at 30 EC for 3 minutes and then programmed to 70 EC at 20 EC/min. The carrier gas consisted of helium (30 ml/min) and a $N_2$ make-up gas. One microliter split samples were analyzed. Retention times of TBA and MTBE were 3 and 3.8 min, respectively.

Results of Substrate Removal Experiments

Results of batch substrate depletion assays with BC-1 in the presence of MTBE are shown in FIG. 1. MTBE (120 mg/liter) was rapidly degraded, within 4 hours at a rate of 34 mg/g of cells per hour. TBA was formed as a transient metabolic product of MTBE breakdown. The highest levels of TBA were reached after MTBE was completely utilized. TBA formed from MTBE declined at a slower rate (14 mg/g of cells per hour) than did MTBE. These results provide evidence that BC-1 degrades MTBE to TBA as a primary and transient intermediate.

PART D: OXYGEN UPDATE EXPERIMENTS

Oxygen uptake rates (OUR) were performed on the BC-1 culture in the presence of substrates and potential metabolic intermediates of MTBE. A Yellow Springs Instrument Company oxygen electrode-water bath assembly (Model 53; 5 ml reaction compartment) was used for these experiments. Suspended solids (TSS) from BC-1 were centrifuged (23, 900×g, 10 min at 4° C.), resuspended to one-half the volume in a sterile phosphate-buffered saline solution, PBS (0.856 NaCl, 0.03M $Na_2HPO_4$ and 0.05M $KH_2PO_4$, pH 7.2). The 2× concentrated culture was aerated (sterile house air) continuously at 30 EC and maintained at a dissolved oxygen level of 6–7 ppm before using in OUR experiments. About 0.01–0.03 g TSS were used in each reaction. Substrates were added at levels of 15 or 50 ppm from sterile stock (1,000 ppm) solutions and oxygen depletion monitored over 3–5 minutes at 30° C. The oxygen electrode and the dissolved oxygen concentration was interfaced and calibrated to the deflection of a lmV recorder (Houston Instrument Company) and rates calculated from the slopes of the tracings. OUR are given as mg oxygen utilized/g TSS/h.

The ability of BC-1 to oxidize MTBE and potential downstream degradation products and other cellular intermediates was determined by oxygen uptake rate (OUR) methods and these data are shown in Table 2. Highest OUR was observed with $NH_4^+$, however, allylthiourea, a specific inhibitor of $NH_4^+$ oxidation, completely blocked this oxygen utilization. MTBE showed two distinct OUR, an initial faster (5.2–5.9 mg $O_2$/g/hr) and a slower (50% less) rate. Addition of allylthiourea had no effect on oxygen utilization in the presence of MTBE. t-Butylformate (TBF, t-butyl-COOH), an intermediate in the reaction of atmospheric-derived chloride and hydroxy free radicals with MTBE also enhanced oxygen uptake in BC-1. t-Butanol, isopropanol and lactate showed comparable OUR to MTBE (4.3–7 mg/g/h).

TABLE 2

Oxygen Uptake Rates (OUR) with Culture BC-1[a]

| Substrate[b] | Net OUR $mgO_2$/g TSS/h |
|---|---|
| $NH_4^+$ | 17.4 |
| $NH_4^+$ + allylthiourea | —[c] |
| Allylthiourea | —[c] |
| MTBE | 5.2–5.9, 2.3[d] |
| MTBE + allylthiourea | 5.2 |
| t-Butylformate (Na) | 7.2 |
| t-Butanol | 6.0 |
| Isopropanol | 4.3 |
| Lactate (Na) | 7.0 |

[a] Continuous culture treating high $NH_4^+$ (120 ppm) and MTBE (150–200 ppm) levels.
[b] All compounds added at 50 ppm.
[c] Less than or equal to the endogeneous OUR.
[d] First and second OUR.

PART E: RADIOLABELED MTBE EXPERIMENTS

The $^{14}CH_3O$-MTBE was custom synthesized by Amersham Corp., (Arlington Heights, Ill.). It had a specific activity of 1.19 F Ci/mg and was 99.3% pure by radiochromatography. Cultures were centrifuged, washed and resuspended in the same volume of sterile PBS buffer (PBS, 0.85% NaCl, 0.03 M $Na_2HPO_4$, 0.05 M $KH_2PO_4$, pH 7.2), and placed in 125 ml serum bottles sealed with TeflonO lined septa. $^{14}CH_3O$-MTBE was added to a concentration of 0.08 F Ci/ml and MTBE at 2 ppm. Cultures were incubated at 300 on a rotary shaker (150–200 rpm) for seven days. The amount of $^{14}CO_2$ formed was determined by placing a 10-ml aliquot of the culture in a similar serum bottle, adjusting the pH to $\leq 2$ with 6N HCl and then flushing the bottle for one hour with a steady stream of $N_2$ into three gas washing bottles containing 0.1M Ba $(OH)_2$. The $Ba^{14}CO_3$ precipitate (formed after co-precipitation with $Na_2CO_3$ addition) was collected onto 0.45 Fm Millipore filters, washed with PBS, dried and the radioactivity was counted. After removal of $^{14}CO_2$, the culture was filtered onto a 0.22 Fm Millipore filter, washed with PBS, dried and counted to estimate $^{14}C$ activity incorporated into biomass (cells). The remaining radioactivity in the filtrate represents undegraded $^{14}CH_3O$-MTBE and/or $^{14}C$-metabolites. The efficiency of trapping $^{14}CO_2$ by this method was confirmed in separate experiments in which $NaH^{14}CO_3$ was added (0.06 microwaves, 70 ppm as $CO_2$) to PBS or azide-inhibited cultures, acidified (pH$\leq$2) and flushed into $Ba(OH)_2$ traps as described. The recovery of $H^{14}CO_3^-$ as $Ba^{14}CO_3$ was 95–100% of the applied radioactivity. The $^{14}C$-radioactivity was determined by placing 1-ml amounts of culture fluid (total $^{14}C$) filtrates or filters containing $Ba^{14}CO_3$ precipitates into glass scintillation vials containing 15 ml Aquasol-2 Universal 2SC Cocktail (NEN Dupont Research Products, Boston, Mass.). Vials were counted in a Packard TRI-CARB (Model 2500 TR) liquid scintillation analyzer (Packard Instrument Co., Meriden, Conn.).

Results of the biodegradation of radiolabeled ether (2 ppm) by BC-1 are given in Table 3. Less than 1% and 5% of the applied isotope was recovered as $^{14}CO_2$ and $^{14}C$-cells, respectively, in the abiotic (no culture) control and cultures containing the respiration inhibitor, sodium azide (2%). About 806 of the $^{14}CH_3O$-MTBE was incorporated into $CO_2$ and cells with the remainder (ca. 15%) as undegraded ether and/or $^{14}C$-metabolites. Addition of 100 ppm $NH_4^+$ to metabolizing cultures had no competitive effect on stimulating or inhibiting MTBE biotransformation.

TABLE 3

Distribution of $^{14}CH_3O$-MTBE in Ether-Degrading Cultures

| | % of Applied $^{14}CH_3O$-MTBE[a] in | | | |
|---|---|---|---|---|
| Condition | $CO_2$ | Cells | MTBE &/or Metabolites | % Recovery |
| 1. Control (no cells) | 0.2 | 4.1 | 13.7 | 18 |
| 2. BC-1[b] + Azide (2%) | 0.9 | 5.1 | 17.1 | 23.1 |
| 3. BC-1 | 39.0 | 42.1 | 17.8 | 98.9 |
| 4. BC-1 + $NH_4^+$ (100 ppm) | 42.3 | 40.3 | 12.5 | 95.1 |

[a]Mean of duplicate cultures did not differ by more than 10%.
[b]Suspended solids as TSS and VSS were 2440 and 1820 ppm, respectively.

Chemicals

Common laboratory chemicals e.g. salts, bases acids, alcohols and ketones used were purchased from Mallinckrodt or Sigma Chemical Companies. MTBE and TBA were obtained as $\geq$98% pure material from Chem. Service Inc. of West Chester, Pa.

PART F: ISOLATION OF PURE CULTURE

Dilution enrichments of the present mixed culture were made to enhance isolation of a specific microbe degrading MTBE. In this method, 10 ml mixed culture enriched from the mixed culture BC-1 from PART A was added to 10 ml sterile Difco Bushnell-Haas ($MgSO_4$, 200 mg/L; $CaCl_2$, 20 mg/; $KH_2PO_4$, 1000 mg/L; $K_2HPO_4$ 1000 mg/L; $NH_4NO_3$ 1000 mg/L; $FeCl_3$, 50 mg/L, pH 7.0) minerals medium (3.5 g/L; referred to as BH) in stoppered serum bottles containing 1–5 mg/L MTBE. At weekly intervals, half of the culture volume (10 ml) was aseptically removed and 10 ml fresh sterile BH medium added to the remaining 10 ml of culture. The dilution enrichment method was continued for at least 2–3 months at 25° C. until a dilute suspension of bacteria degrading MTBE consistently degraded MTBE before each transfer interval. This dilution enrichment culture was subsequently streaked onto sterile Petri plates containing BH minerals plus 1.5% Difco Agar as solidifying agent. Plates were incubated at 25° C. or 30° C. and observed for the appearance of colonies after 3–5 days. Approximately 20 colonies were picked with sterile needles and inoculated into 20 serum vials containing sterile PH medium and 1–10 mg/L MTBE. These cultures were incubated at 25–30° C. and the loss of MTBE from the headspace of serum vials was determined. One isolates (10 BC) completely degraded MTBE without the appearance of intermediates such as t-butyl alcohol.

PART G. DEGRADATION OF MTBE BY PURE CULTURE

The pure culture isolate 10BC was grown in $R_2A$ broth medium (yeast extract 0.5 g/L; peptone 0.5 g/L; casein acid hydrolyzate, 0.5 g/L; soluble starch, 0.5 g/L; glucose 0.5 g/L; $KH_2PO_4$, 0.3 g/L; $MgSO_4$, 0.024 g/L; solidum pyrovate, 0.3 g/L; pH 7.0) for 24–48 hours at 25° C. The culture was then centrifuged (8000 rpm, 15 min.) and resuspended into 10 ml sterile phosphate-buffered saline (NaCl, 9 g/L; $KH_2PO_4$, 6.85 g/L; pH 7.0–7.2). The culture was transferred to a 30 ml serum vial. MTBE added to a concentration of 5 mg/L and stoppered and sealed. The degradation of MTBE was followed at 25° C. over several days. Table 4 is an example of MTBE degraded by this pure culture from 5 mg/L to non-detectable concentrations (5 μg/L) in 48 hours (Run #1). This culture was respiked with 5 mg/L MTBE. MTBE was degraded 95% (0.24 mg/L) in 27 hours (Run #2 Table 5).

TABLE 4

| Run #1: Degradation of MTBE by Pure Culture | |
|---|---|
| Initial MTBE mg/L | MTBE after 48 hours |
| 5 | 0.005 |

TABLE 5

| Run #2: Degradation of MTBE by Pure Culture | |
|---|---|
| Initial MTBE mg/L | MTBE after 27 hours |
| 5 | 0.24 |

PART H: PHYSIOLOGICAL PROPERTIES OF PURE CULTURE

Table 6 summarizes some physiological properties and substrates utilized by one of the MTBE-degrading isolates, 10BC. The organism is an aerobic gram-positive rod-shaped bacterium that grows well on few sugars (e.g. sucrose), several acids (acetate, monomethyl-succinate, gluconate, cis-aconitate, 1-ketoglutanate, saccharate, gamma-aminobutyrate, urocanate) and amino acids (aspartate, glutamate, hydroxy-proline, proline and arginine). 10BC also grows well on the metabolic intermediates in the MTBE pathway, namely, isopropanol, acetone and acetate. However, the isolate grows poorly on MTBE and t-butyl alcohol as shown above with the BC-1 mixed culture consortium. Growth of 10BC on aromatic hydrocarbons (benzene, toluene, ethylbenzene and xylene) was also poor but good growth was observed on the saturated alkane hydrocarbon, hexadecane. The culture grows well on a variety of complex bacteriological media including Trypticase Soy Broth and Agar (BBL, Becton Dickinson, Inc.) and Plate Count Agar (Difco). Based on physiological and biochemical features of 10BC as a non-fermentative gram-positive, oxidase-negative, catalase-negative bacterium and substrate utilization patterns in the Oxi/Ferm and Biolog assays and characteristics described in Bergey's Manual of Systematic Bacteriology, it is possible (but by no means limited to) that this isolate may belong to the genera Corynebacterium, Actinomycetes, Nocardia or Mycobacterium. A bacterial ribonsomal RNA sequence analysis for identification of genus provides confirmation of the identity of the pure culture.

TABLE 6

Physiological features & substrates utilized by pure culture isolate 10BC

| FEATURE | REACTION |
|---|---|
| Morphology | Medium rod (0.5–1.0 Micron diam.), non-motile |
| Gram stain | Positive |
| Pigment formed | Light yellow (intracellular) orange |
| Oxidase reaction | Negative[a] |
| Optimum growth temp. | 20–35° C.; strict aerobe |
| Catalase | Negative |
| Substrates utilized Biolog assay[b] | between 40, monomethyl succinate cis-aconitric acid, L-saccharic acid, D-gluconic acid, D-gluconic acid, alanyl-glycine, L-aspartic acid L-acid, L-histidine, hydroxy L-proline, L-proline, gammo-amino butyric acid, uraocanic acid, ketoglutaric acid, glutamic acid |
| Substrates utilized oxi/ferm Tube[c] | Arginine, xylose, glucose, citrate |
| Other substrates utilized[d] | Acetate, isopropanol, acetone hexadecane |
| Weak growth substrates[d] | MTBE, t-butyl alcohol, benzene toluene ethylenebenzene, m-xylene |

[a]Oxidase reaction negative with growth on some substrates.
[b]Biolog Identification System GN Plate (Biolog, Inc; Hayward, CA) a carbon source utilization method for identification of gram-negative bacteria. Multimedia substrate utilization tube for identification of oxidative-fermentative gram-negative rods (Hoffman-La Roche, Inc.); Miller, & Rhoden, 1991.
[c]Substrates tested in the Oxi/Ferm tube include glucose, xylose, urea, citrate and arginine.
[d]Substrates were added to sterile (Bushnell Haas) medium at concentrations of 100–200 mg C/L and growth evaluated after inoculating media with 1 ml of acetate-grown (24 hour) culture of 10BC-3 and determining visual growth after incubating at 30° C. for 3–7 days.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

What is claimed is:

1. A process for degrading MTBE in an MTBE-containing mixture, which process comprises adding to said MTBE-containincg mixture a pure bacterial culture obtained from a mixed bacterial culture having the identifying characteristics of mixed bacterial culture ATCC No. 202057, wherein said pure bacterial culture degrades methyl-t-butyl ether (MTBE) to carbon dioxide within 70 hours; wherein said pure culture is obtained by a process comprising the steps of:
    (a) enhancing the isolation of said pure bacterial culture from said mixed bacterial culture by a dilution enrichment process using MTBE and sterile nutrients-containing medium to obtain a dilute enrichment of said mixed culture,
    (b) transferring a portion of said dilute enrichment of said mixed culture from (a) to a sterile container comprising nutrients and solidifying agent,
    (c) incubating said container from (b) above to obtain colonies of bacteria;
    (d) transferring a portion of a colony from (c) above to a container and incubating it in presence of sterile nutrients and MTBE for a period of time to produce colonies, and
    (e) repeating step (d) until one of the colonies degrades MTBE to carbon dioxide within 70 hours after said incubating step of (d) above.

2. The process as described in claim 1, wherein said pure bacterial culture also degrades t-butyl alcohol.

3. A process for simultaneously degrading MTBE and TBA in a MTBE and TBA-containing mixture, which process comprises adding to said MTBE and TBA-containing mixture a pure bacterial culture obtained from a mixed bacterial culture having the identifying characteristics of mixed bacterial culture ATCC No. 202057; wherein said pure bacterial culture degrades both MTBE and TBA to carbon dioxide within 70 hours, and said pure bacterial culture is prepared by a process comprising the steps of:
    (a) enhancing the isolation of said pure bacterial culture from said mixed bacterial culture by a dilution enrichment process using MTBE and sterile nutrients-containing medium to obtain a dilute enrichment of said mixed culture,
    (b) transferring a portion of said dilute enrichment of said mixed culture from (a) to a sterile container comprising nutrients and solidifying agent,
    (c) incubating said container from (b) above to obtain colonies of bacteria;
    (d) transferring a portion of a colony from (c) above to a container and incubating it in presence of sterile nutrients and MTBE for a period of time to produce colonies, and
    (e) repeating step (d) until one of the colonies degrades MTBE and TBA to carbon dioxide within 70 hours after said incubating step of (d) above.

4. A pure bacterial culture obtained from a mixed bacterial culture having the identifying characteristics of mixed bacterial culture ATCC No. 202057; wherein said pure bacterial culture degrades methyl-t-butyl ether (MTBE) to carbon dioxide within 70 hours; wherein said pure culture is obtained by a process comprising the steps of:
    (a) enhancing the isolation of said pure bacterial culture from said mixed bacterial culture by a dilution enrichment process using MTBE and sterile nutrients-containing medium to obtain a dilute enrichment of said mixed culture,
    (b) transferring a portion of said dilute enrichment of said mixed culture from (a) to a sterile container comprising nutrients and solidifying agent,
    (c) incubating said container from (b) above to obtain colonies of bacteria;
    (d) transferring a portion of a colony from (c) above to a container and incubating it in presence of sterile nutrients and MTBE for a period of time to produce colonies, and
    (e) repeating step (d) until one of the colonies degrades MTBE to carbon dioxide within 70 hours after said incubating step of (d) above.

5. The pure bacterial culture as described in claim 4, wherein said dilution enrichment process in step (a) comprises the following steps:
   (i) adding said mixed bacterial culture having said identifying characteristic of mixed bacterial culture ATCC No. 202057 to a sterile nutrient medium containing MTBE to form a first enrichment,
   (ii) incubating for a period of time, periodically testing for MTBE degradation, after degradation of MTBE is proven, aseptically removing a portion of incubated first enrichment to obtain a remainder portion of incubated said first enrichment,
   (iii) adding a fresh portion of a sterile nutrient medium to said remainder portion of incubated first enrichment to form a second enrichment,
   (iv) incubating said second enrichment for a period of time, periodically testing for MTBE degradation, after degradation of MTBE is proven, aseptically removing a portion of incubated second enrichment to obtain a remainder portion of incubated second enrichment,
   (v) adding a fresh portion of said sterile medium to said remainder portion of incubated second mixture to form a third enrichment, and
   (vi) repeating the dilution steps of (iv) and (v), to obtain a dilute enrichment of bacteria, which degrades MTBE.

6. The pure culture as described Win claim 4, wherein said pure culture also degrades t-butyl alcohol.

* * * * *